United States Patent [19]

Papajohn

[11] 4,044,769

[45] Aug. 30, 1977

[54] PANTY WITH SANITARY NAPKIN HOLDER

[76] Inventor: Elissa D. Papajohn, 65 Montague St., Brooklyn, N.Y. 11201

[21] Appl. No.: 506,229

[22] Filed: Sept. 16, 1974

[51] Int. Cl.² .............................................. A61F 13/16
[52] U.S. Cl. .................................... 128/288; 128/284; 128/290 R
[58] Field of Search ........... 128/284, 288, 287, 290 R, 128/290 H, 291, 526

[56] References Cited
U.S. PATENT DOCUMENTS

| 1,041,420 | 10/1912 | Bornstein | 128/289 |
| 1,233,811 | 7/1917 | Roger | 128/289 |
| 1,967,859 | 7/1934 | Burns | 128/290 R |
| 2,102,359 | 12/1937 | Frieman | 128/289 |
| 2,977,957 | 4/1961 | Clyne | 128/291 |
| 2,985,170 | 5/1961 | Title | 128/284 |
| 3,460,535 | 8/1969 | Behna | 128/288 |

Primary Examiner—Aldrich F. Medbery
Attorney, Agent, or Firm—Bauer, Amer & King

[57] ABSTRACT

A panty-type garment having a fluid-tight compartment for conveniently supporting an absorbent material therein, as a sanitary napkin, whereby the napkin is exposed through an opening to receive fluids discharged from the body of the user to which the garment is applied and restrained from relative movement.

1 Claim, 7 Drawing Figures

U.S. Patent     Aug. 30, 1977     4,044,769
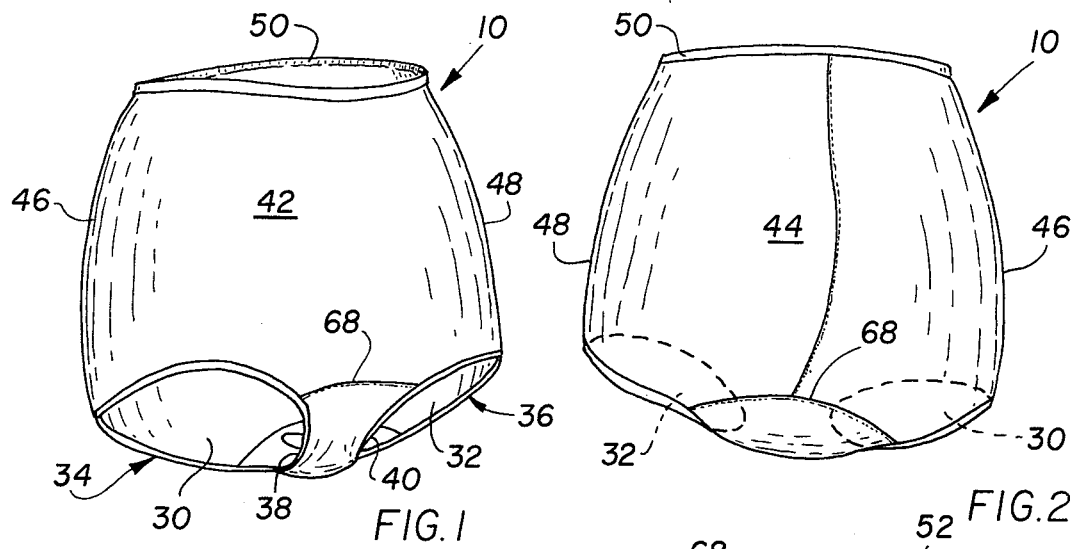
FIG. 1
FIG. 2
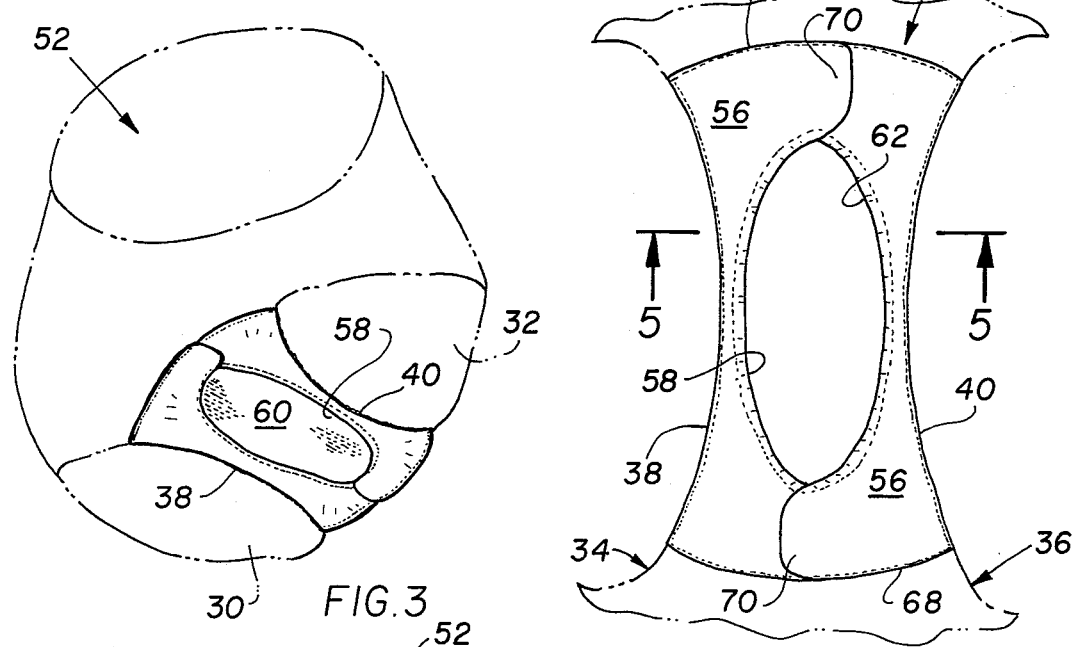
FIG. 3
FIG. 4
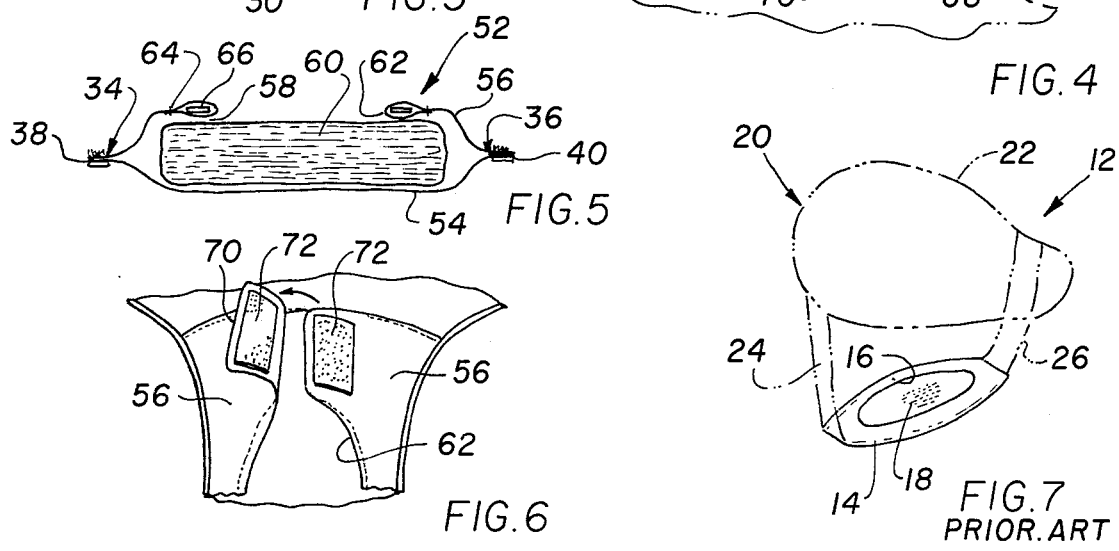
FIG. 5
FIG. 6
FIG. 7 PRIOR ART

PANTY WITH SANITARY NAPKIN HOLDER

The present invention relates to an improved sanitary napkin holder, and more particularly to improved means for the effective sealed confinement of the napkin during an interval of use.

It is already well known, according to the sanitary napkin holder of U.S. Pat. No. 3,079,922, that ease and comfort during the use of a sanitary napkin can be effectively promoted by suspending the holder from an appropriate belt or harness. This type support, however, detracts from fluidtight confinement of the napkin, which is an equally important requirement.

Broadly, it is an object of the present invention to provide an effectively sealed sanitary napkin holder overcoming the foregoing and other shortcomings of the prior art. Specifically, it is an object to embody the holder in a panty so as to utilize the elastic thereof, particularly about the leg openings, to contribute to the sealing of the napkin.

A panty with a built-in sanitary napkin holder demonstrating objects and advantages of the present invention is one having a front, rear and opposite sides cooperating to define a lower torso garment having an upper elasticized waist opening and right and left elasticized leg openings. A sanitary napkin compartment is formed of two fluid-tight plies disposed in facing, superposed relation to each other in the crotch area of the panty. The compartment is oriented to extend between the front and rear of the panty and in spanning relation between the elasticized leg openings, such that length portions of the elastics of the leg openings form the opposite side edges of the compartment. In this manner, gripping contact of the elastic length portions is established with the user's legs to contribute to an optimum sealed confinement of the sanitary napkin in said compartment during wearing service of the panty.

The above brief description, as well as further objects, features and advantages of the present invention, will be more fully appreciated by reference to the following detailed description of a presently preferred but nonetheless illustrative embodiment in accordance with the present invention, when taken in conjunction with the accompanying drawings, wherein:

FIG. 1 is a front elevational view of a panty embodying the present invention;

FIG. 2 is a rear elevational view of said panty;

FIG. 3 is a diagrammatic view of the sanitary napkin compartment of the panty, the other portions of the panty being illustrated in phantom perspective to better illustrate said compartment;

FIG. 4 is a partial view, on an enlarged scale, of the sanitary napkin compartment;

FIG. 5 is a side elevational view, in section taken on line 5—5 of FIG. 4, illustrating further structural details of the compartment;

FIG. 6 is a partial detailed view illustrating the flap of the compartment; and

FIG. 7 diagrammatically illustrates a typical prior art sanitary napkin holder, which the within panty is intended to replace.

As a preliminary to the description of the improved panty 10 of the present invention, as illustrated in FIGS. 1-6, reference should first be made to the diagramatic illustration in FIG. 7 of a typical prior art sanitary napkin holder 12. As generally understood, and as is set forth in the description of the holder 12 in prior U.S. Pat. No. 3,079,922, holder 12 includes a construction 14 which is located in the area coextensive with the crotch of the user and includes fabric or plastic plies appropriately stitched together so as to form a compartment 16 for a sanitary napkin 18. After placement of the napkin 18 in the compartment 16, the napkin holder or construction 14 is held in proper location on the user by an appropriate harness 20 which typically includes an elastic waist-encircling strap 22 and front and rear connecting members 24 and 26. During wearing service of the prior art sanitary napkin holder 12, it is contemplated that vaginal discharge will be absorbed by the sanitary napkin 18 by virtue of the communication established with the napkin 18 through the compartment opening 16.

As an improvement over a harness-supported sanitary napkin holder, as exemplified by the holder 12, it is proposed, according to the present invention, to use the panty 10 of FIGS. 1-6. One of the important aspects of the present invention is the recognition that structural aspects of the panty 10 can be effectively utilized to significantly contribute to the ability of a holding structure to contain a sanitary napkin in fluid tight condition. Specifically, as is well understood, the construction of a panty 10 includes right and left leg openings 30 and 32 which have elastic material stitched along the edges bounding these openings, as at 34 and 36. As will be explained in detail subsequently, the length portions 38, 40 of the elastics 34, 36 respectively, which are strategically located along the marginal edges of the crotch area of the panty, are utilized as the side edges of the compartment for the sanitary napkin. Thus, during wearing service of the panty 10, a firm, practically fluid-tight gripping contact is established between the elastic lengths 38 and 40 and the user's legs, and such contact has been found to contribute to an optimum sealed confinement of the sanitary napkin in the compartment during wearing service of the panty, all as will now be described in detail.

Panty 10, as generally understood, includes elastic fabric which is cut to pattern so as to provide a front 42, a rear 44, and opposite sides 46 and 48. In a well understood manner, the aforesaid cooperate to define a garment which is adapted to fit the lower torso. In addition to the already noted elasticized leg openings 30 and 32, panty 10 also includes an elasticized waist opening 50.

In accordance with the present invention, a sanitary napkin holder, generally designated 52 in FIGS. 3, 4 and 5, is effectively incorporated as a part of the panty 10. Holder 52, in the preferred form illustrated, is fabricated out of waterproof material, preferably polyurethane, and consists of upper and lower plies 54, 56 arranged in superposed relation to each other and appropriately secured together to form a sanitary napkin compartment 58. As is perhaps best illustrated in FIGS. 4, 5, one effective way of joining together the plies 54 and 56 is to catch these two plies in the seam which applies the elastic loops 34 and 36 about the leg openings 30 and 32. This is readily done on a high post sewing machine or the like.

As already noted, since the holder 52 extends the entire width of the crotch area of the panty 10, or stated another way, is of a width which spans the distance between the leg openings 30 and 32, it effectively utilizes the elastic length portions 38 and 40 of these leg openings as its side edges. Also as already noted, these elastic sides 38, 40 contribute to the establishment of a fluid-tight seal with the user's legs and, in turn, contribute to an effective fluid-tight confinement of the sanitary napkin.

Preparatory to use of the panty 10, a conventional absorbent sanitary napkin 60 is placed in the compartment 58. To establish communication for the napkin 60, the upper ply 56, as best illustrated in FIG. 4, has an oval opening 62. To assist in confining napkin 60 within compartment 58, the edge bounding the opening 62 is folded into a hem 64 and an elastic 66 is inserted in the hem and stitched in place (see in particular FIG. 5). The hem 64 minimizes chafing contact of the elastic 66 against the user.

From the description thus far, it should be apparent that the proper location for the holder 52 is in the area coextensive with the crotch area of the panty 10. To provide this position, as already noted the opposite sides of the holder 10 form a part of the leg openings 30 and 32, and the front and rear of the holder are respectively stitched, as at 68, to the front and rear panels of the panty 10.

To facilitate removal of the napkin 60, provision is made for enlarging the oval opening 62 of compartment 58. Specifically, as illustrated in FIGS. 4, 6, at each of the opposite ends of the opening 62 a tab or flap 70 is formed in the upper ply 56. Velcro, in patch shapes 72, are appropriately secured in facing relation to each other on flap 70 and in the area of the ply which is beneath the flap, to thereby form a closure for the opposite ends of the oval opening 62 which can be opened to enlarge the opening incident to removing the pad 60.

From the foregoing it should be readily appreciated that there has been described herein a sanitary napkin holder 52 embodied in the construction of a panty 10 so as to effectively utilize the elasticized portion of the panty to contribute to more effective fluid-tight confinement of the sanitary napkin.

A latitude of modification, change and substitution is intended in the foregoing disclosure, and in some instances some features of the invention will be employed without a corresponding use of other features. Accordingly, it is appropriate that the appended claims be construed broadly and in a manner consistent with the spirit and scope of the invention herein.

For ease of explanation reference has been made herein to a panty-type garment. Those skilled in the art will readily recognize that such articles of wear may include garments that are made without legs such as is illustrated and has been previously described and with legs or leg receiving openings, as leotards, panty-hose, and the like. Such panty type garments have a form fit engagement with the desired lower torso and thus inhibit shifting or movement of the compartment opening relative to the body opening from which the fluid discharge is received.

What is claimed is:

1. In combination, a panty and the like having a front, rear and opposite sides cooperating to define at least a lower torso garment having a waist opening and edges bounding right and left leg openings, elastic secured along said waist and leg openings to urge said edges of the latter into gripping contact with the user's legs to contribute to an optimum sealed confinement for a sanitary napkin during wearing service of said panty, and a sanitary napkin compartment formed of plies of fluid-tight material disposed in facing, superposed relation to each other in the crotch area of said panty, said compartment being oriented to extend between the front and rear of said panty and in substantial spanning relation between said elasticized leg openings, said compartment being further adapted to receive as a sanitary napkin a fluid absorbent material that is exposed to the interior of said panty through an opening defined in one of said plies in the interior of said panty, said opening extending for a substantial portion of the length of said compartment and for a width of said compartment sufficient to receive fluids discharged from the body of the user without side leakage from said compartment, and elastic secured along said compartment opening oriented substantially parallel to the elastic of said leg openings to retain the sides of said compartment opening about the absorbent material in said compartment without adverse effect on said seal of said elasticized leg openings, said panty supporting said compartment in position on the user such that the opening is restrained from movement relative to the body so that the compartment opening will remain in position to enable the absorbent material to receive the discharged body fluids.

* * * * *